(12) United States Patent
Atkins et al.

(10) Patent No.: US 8,251,975 B2
(45) Date of Patent: Aug. 28, 2012

(54) CATHETER AND TUNNELING DEVICE THEREFOR

(76) Inventors: Joseph R. Atkins, Vandalia, OH (US); David George Catlin, Heath, TX (US)

(*) Notice: Subject to any disclaimer, the term of this patent is extended or adjusted under 35 U.S.C. 154(b) by 91 days.

(21) Appl. No.: 12/683,560

(22) Filed: Jan. 7, 2010

(65) Prior Publication Data
US 2010/0174291 A1     Jul. 8, 2010

Related U.S. Application Data

(63) Continuation of application No. 11/460,534, filed on Jul. 27, 2006, now abandoned, and a continuation-in-part of application No. 29/244,662, filed on Dec. 13, 2005, now Pat. No. Des. 542,414, and a continuation-in-part of application No. 11/161,212, filed on Jul. 27, 2005, now abandoned.

(51) Int. Cl.
*A61M 31/00* (2006.01)
*A61M 5/178* (2006.01)
*A61M 5/32* (2006.01)
*A61M 5/00* (2006.01)
*A61M 25/00* (2006.01)

(52) U.S. Cl. ........ 604/510; 604/506; 604/507; 604/508; 604/158; 604/160; 604/161; 604/162; 604/264; 604/266; 604/268; 604/528

(58) Field of Classification Search .......... 604/158, 604/160, 161, 162, 163, 164.01, 164.07, 604/165.01, 165.02, 165.04, 166.01, 264, 604/272, 500, 506, 507, 508, 510, 93.01, 604/164.08, 266, 268, 523, 528, 284; 606/108
See application file for complete search history.

(56) References Cited

U.S. PATENT DOCUMENTS

| | | | |
|---|---|---|---|
| 3,598,118 A * | 8/1971 | Warren | 604/508 |
| 3,827,434 A * | 8/1974 | Thompson et al. | 604/160 |
| 4,068,659 A * | 1/1978 | Moorehead | 604/508 |
| 4,100,246 A | 7/1978 | Frisch | |
| 4,430,081 A | 2/1984 | Timmermans | |
| 4,432,752 A * | 2/1984 | Marlon | 604/500 |
| 4,504,268 A | 3/1985 | Herlitze | |
| 4,613,329 A * | 9/1986 | Bodicky | 604/158 |
| 4,619,643 A | 10/1986 | Bai | |
| 4,961,809 A | 10/1990 | Martin | |
| 4,981,471 A | 1/1991 | Quinn et al. | |
| 5,053,004 A | 10/1991 | Markel et al. | |
| D328,128 S | 7/1992 | Fox et al. | |
| 5,374,245 A | 12/1994 | Mahurkar | |
| 5,472,432 A | 12/1995 | Martin | |

(Continued)

*Primary Examiner* — Kevin C Sirmons
*Assistant Examiner* — Shefali Patel
(74) *Attorney, Agent, or Firm* — R. William Graham (57) ABSTRACT

A catheter for introduction and removal of fluids from a body and tunneling device therefor, the catheter has a body having a first conduit for removing fluid from the body and a second conduit for delivering fluid to the body wherein at least a part of each of the conduits is integrally formed within a first end of the body of the catheter and extends along side one another. The first conduit extends beyond the second conduit and forms a terminal point of the first end and defines a first opening thereat and the second conduit extends to a point short of the terminal point defining a second opening. A bumper portion is adjacent the second opening extending toward the terminal point. Another part of each the first and the second conduits are disjoined and form part of a second Y-shaped end. The tunneling device has a channel to removably receive the catheter.

4 Claims, 6 Drawing Sheets

U.S. PATENT DOCUMENTS

| | | |
|---|---|---|
| 5,509,897 A | 4/1996 | Twardowski et al. |
| 5,545,136 A * | 8/1996 | Berger ................... 604/96.01 |
| 5,665,093 A | 9/1997 | Atkins et al. |
| D384,741 S | 10/1997 | Musgrave et al. |
| 5,817,060 A | 10/1998 | Overton et al. |
| D405,525 S | 2/1999 | Barrett et al. |
| D467,657 S | 12/2002 | Scribner |
| 6,565,589 B1 | 5/2003 | Jervis et al. |
| 6,595,966 B2 | 7/2003 | Davey et al. |
| 6,638,242 B2 | 10/2003 | Wilson et al. |
| 6,749,580 B2 | 6/2004 | Work et al. |
| 6,758,836 B2 | 7/2004 | Zawacki |
| D504,508 S | 4/2005 | Patrickson |
| 6,911,014 B2 | 6/2005 | Wentling et al. |
| 2003/0018322 A1* | 1/2003 | Tanghoj et al. ............... 604/544 |
| 2004/0044348 A1* | 3/2004 | Skakoon ................... 606/108 |
| 2004/0065333 A1 | 4/2004 | Wilson et al. |
| 2005/0096585 A1 | 5/2005 | Schon et al. |
| 2005/0209582 A1 | 9/2005 | Quinn et al. |
| 2006/0009783 A1* | 1/2006 | Rome et al. ................... 606/108 |
| 2006/0184097 A1 | 8/2006 | Quinn |
| 2007/0016124 A1 | 1/2007 | McGraw |

* cited by examiner

CATHETER AND TUNNELING DEVICE THEREFOR

CROSS-REFERENCE TO RELATED APPLICATIONS

This application is a continuation of application Ser. No. 11/460,534, filed Jul. 27, 2006 now abandoned, entitled CATHETER AND TUNNELING DEVICE THEREFOR, and a continuation-in-part of application Ser. No. 11/161,212, filed Jul. 27, 2005 now abandoned, entitled CATHETER AND TUNNELING DEVICE THEREFOR, and Ser. No. 29/244,662, filed Dec. 13, 2005 now U.S. Pat. No. Des. 542,414, entitled TUNNELING DEVICE FOR A CATHETER, both commonly assigned to the assignee of the present application, the disclosures of which are incorporated by reference in their entirety herein.

FIELD OF INVENTION

The present invention relates to catheters and more particularly to an improved catheter for introduction and removal of fluids from a body and to a tunneling device to more readily enable insertion of the catheter.

BACKGROUND OF THE INVENTION

Medical catheters have been used successfully for many years to access the blood stream of human and animal patients. Multi-lumen catheters are used for a variety of applications where it is necessary to have two or more separate fluid pathways. The purposes of accessing the blood circulatory system include introduction of medication, hemodialysis therapy, plasmaphoresis therapy, and other therapies which may require access to the blood circulatory system.

In the case of hemodialysis, a dual-lumen catheter can be employed to simultaneously accommodate opposing blood flow. One lumen aspirates blood from a blood vessel of a patient to a dialysis machine where it is processed for the removal of toxins, while the other lumen infuses the purified blood to the patient.

A problem in many dialysis catheters is clotting and fibrin sheath formation around the "arterial" inlet used for aspiration of blood from a patient. Thrombus and fibrin can occlude distal tips or other places throughout the length of the catheter lumens, resulting in loss of catheter function when such an occlusion prevents blood flow. Usually, catheters have one large exposed hole or one large hole with many little side holes. The thought process is that the extra holes will prevent the inlet from sucking up against the blood vessel wall. Unfortunately, the small holes become filled with fibrin and the large inlet hole develops a trap door clot, which makes the catheter useless. A secondary problem is that related to the arterial lumen "sucking" against the vessel wall in which it resides. This problem can occur if the arterial lumen ports become fully occluded by the patient's vasculature. A technique to resolve such problem is to reverse the bloodlines (i.e., to aspirate through the longer lumen, and to infuse through the shorter lumen, contrary to normal therapeutic pump blood flow). This causes cleaned blood to flow directly toward the lumen that is under vacuum, line reversal in certain catheters can result in inefficient flow and (high re-circulation).

Additionally, there are major side effects which carry patient safety issues, such as hemorrhaging due to the use of indwelling anticoagulants. These anticoagulants are used when the catheter is not being utilized. Side effects of these anticoagulants, primarily heparin, cause acute and chronic gastrointestinal bleeding, retinopathy, and anemia.

Another major issue is that of infection. Currently, catheters on the market use only one single cuff immediately beneath the skin, which is expected to anchor the catheter into the patient's tissue, as well as provide blockage to motile bacteria. This cuff design is often inadequate to perform these functions.

The present invention solves many of the above problems associated with catheters as will become apparent in reading the following hereinafter.

SUMMARY OF THE INVENTION

A feature of the present invention is to provide a catheter to ensure safe access to the blood circulatory system of humans and animals.

Another feature of the invention is to enable catheter access to the blood circulatory system of humans and animals without the need for an indwelling anticoagulant.

Yet another feature of the invention is to provide a catheter inlet which is substantially less prone to be blocked off as a result of sucking up against the blood vessel wall.

A further feature of the invention is to provide a catheter that has the ability to substantially prevent clotting of the lumens of the catheter without the need of clot busting agents.

Another feature of the invention is to provide a catheter with the ability to reduce long term infections that accompany long term placement of central venous lines.

A further feature of the invention is to improve long term health benefits for hemodialysis and plasmaphoresis patients with improved blood flow rates.

Yet another feature of the invention is to provide a catheter that can safely access the blood circulatory system of humans and animals with minimal risk of air embolism.

Accordingly, the present invention is directed to a catheter for introduction and removal of fluids from a body and a tunneling device to more readily enable insertion thereof. In one embodiment, the catheter includes a first lumen for removing fluid from the body and a second lumen for delivering fluid to the body wherein at least a part of each of the lumens is integrally connected within a first end of a catheter body and extends along side one another. The connected part of the first lumen, preferably the fluid delivering lumen, extends beyond the second lumen and forms a terminal point of the first end of the catheter and defines a first opening thereat. The connected part of the second lumen, preferably the fluid receiving lumen, extends to a point short of the terminal point and defines a second opening. Also, a bumper portion, which can preferably be tapered, is integrally formed onto the first end adjacent the second opening and extends toward the terminal point.

The first and second lumens each have another part which is disjoined at a joint to a second Y-shaped end of the catheter. Each disjoined part of each includes a terminal end defining and opening. Each end can preferably be fitted with a Luer lock fitting.

A first flexible obturator rod is provided and is of a size and length to extend through the first conduit in a slidably sealable manner and is equipped with an end cap which is configured to sealably connect to the Luer lock fitting of the first lumen. A second flexible obturator rod is provided and is of a size and length to extend through the second lumen in a slidably sealable manner and is equipped with an end cap which is configured to sealably connect to the Luer lock fitting of the second lumen. A clamp is operably disposed about each of the lumens.

The first end can include one or more longitudinally spaced cuffs which provide for tissue ingrowth therein to enable the catheter to be suitably anchored within the body. A visible indicia can preferably be formed on the first end between the cuffs and the second end to serve as a position indicator of the cuffs.

In addition, the present invention provides for a tunneling device for use in inserting the catheter. In one embodiment, the tunneling device includes a relatively rigid member having a handle and an end which is of a length longer than the first end of catheter and is configured with an exposed elongated channel to receive the first end of the catheter. The tunneling device end is equipped with a hollow cap to receive the openings of the first end of the catheter in a manner to maintain the openings substantially covered during insertion of the catheter into the body thereby preventing potential clogging thereof by tissue and blood. The channel can be generally oval shaped to contain the connected conduit parts of the catheter. Further, the tunneling device can include a mid-section having a Y-shaped exposed channel continuous with the exposed elongated channel to receive at least part of the Y-shaped joint of the catheter.

A method of introducing the catheter into a body is also provided. Further features and advantages of the present invention will become apparent from the following description and drawings.

BRIEF DESCRIPTION OF THE DRAWINGS

The invention is illustrated in the drawings in which like reference characters designate the same or similar parts throughout the figures of which.

DETAILED DESCRIPTION OF THE PREFERRED EMBODIMENTS

Referring now to the drawings, the present invention in one exemplary embodiment is generally directed to a catheter 10 for introduction and removal of fluids from a body B and a tunneling device 12 to more readily enable insertion of the catheter 10. The catheter 10 includes a first lumen 14 for removing fluid from the body B and another lumen 16 for delivering fluid to the body. The lumens 14 and 16 include distal lumen segments 18, 20, respectively, which are integrally connected as part of a first end 22 of the catheter 10 and extend along side one another. Preferably, the catheter 10 is made of a biologically inert, somewhat flexible, material, such as, but not limited to, a urethane or polyurethane-based material, such as CARBOTHANE® (available from Thermedics Corp.), polyether block amides, such as PEBAX® (available from Arkema Inc.) or other material known to those skilled in the art that possesses sufficient bioinertness, durability, flexibility and moldability or extrudability.

Figures 1, 2, 3, 4, 5, 6A:
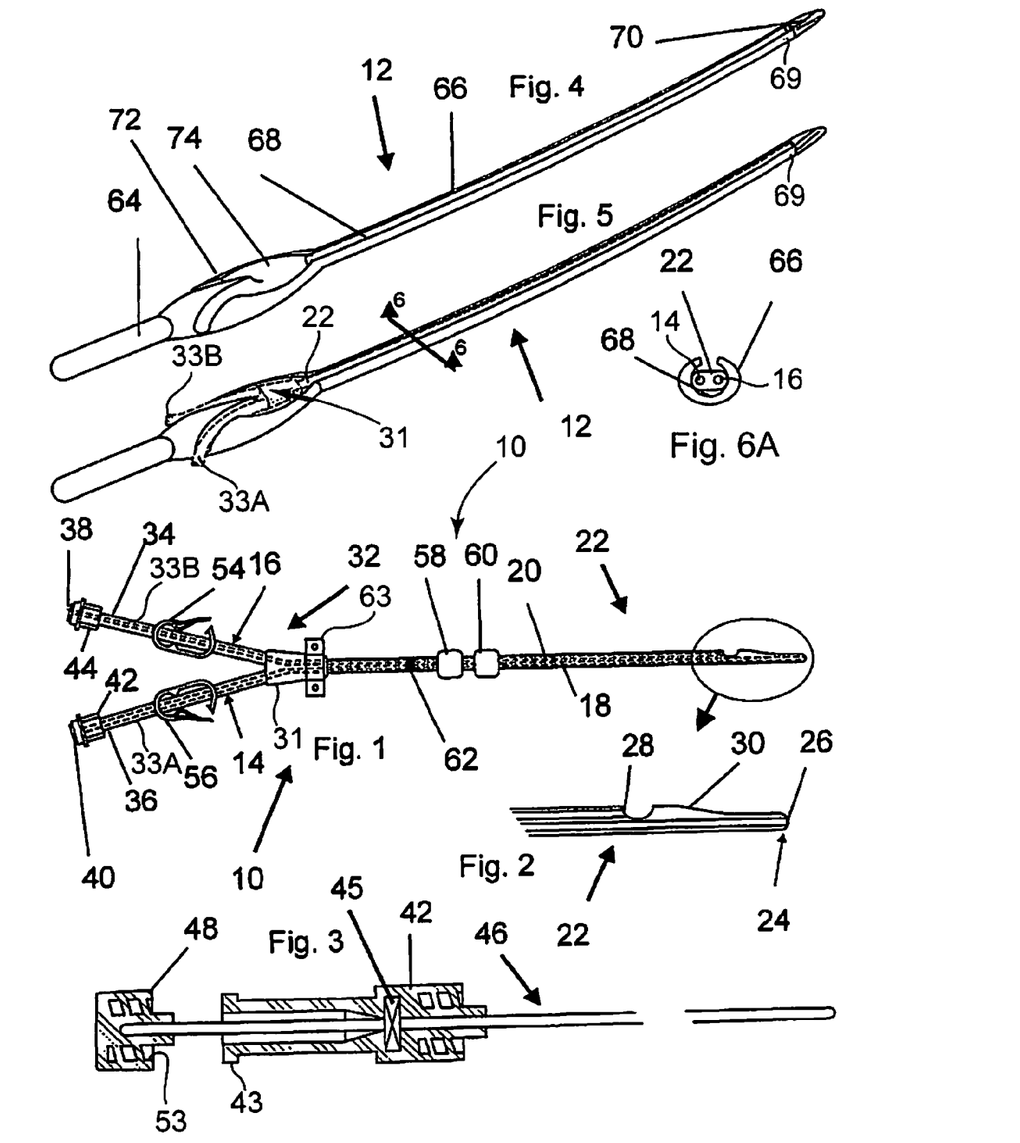
FIG. 1 shows one exemplary embodiment of a catheter of the present invention.
FIG. 2 shows an end portion of the catheter of FIG. 1.
FIG. 3 shows a flexible rod for use in the catheter of FIG. 1.
FIG. 4 shows one exemplary embodiment of a tunneling device of the present invention.
FIG. 5 shows the tunneling device in FIG. 4 with the catheter of FIG. 1 disposed therein.
FIG. 6A-6D show cross-sections along line 6-6 of FIG. 5 and alternative cross-section shapes of the catheter.

The first lumen 14 can be the fluid delivering conduit (arterial flow) which extends beyond the second lumen 16 as best seen in FIGS. 1 and 2 and forms a terminal point 24 of the distal first end 22 and defines a first opening 26 thereat. The second lumen 16 can preferably be the fluid receiving conduit (venous flow) which extends to a point short of the terminal point 24 and defines a second opening 28. It is to be understood that the first lumen 14 could be used for venous flow and the second lumen 14 used for arterial flow. For illustrative purposes for the description below of the alternative lumen embodiments, lumen 14 will be described as the arterial lumen and lumen 16 described as the venous lumen. Also, a bumper portion 30, which can preferably be tapered, is integrally connected to the first end 22 adjacent the second opening 28 and extends toward the terminal point 24 (other bumper and tip configurations are discussed hereinbelow). The external surface of the catheter 10 (and/or the internal lumen walls) which is inserted into the body may have a bioactive material, such as a drug, protein or other material or materials, coated, impregnated or otherwise associated with the surface. In such a case the surface of the catheter may be treated to make association of the bioactive material with the wall more efficient. Such bioactive materials as well as surface materials and treatments are known to those skilled in the art and the present invention also contemplates adapting the catheter 10 to be able to use new bioactive materials and coating techniques developed hereafter.

FIG. 6A shows a cross section of the catheter 10 showing a circular cross-section lumen configuration with each lumen being approximately the same size.

Figure 6B:
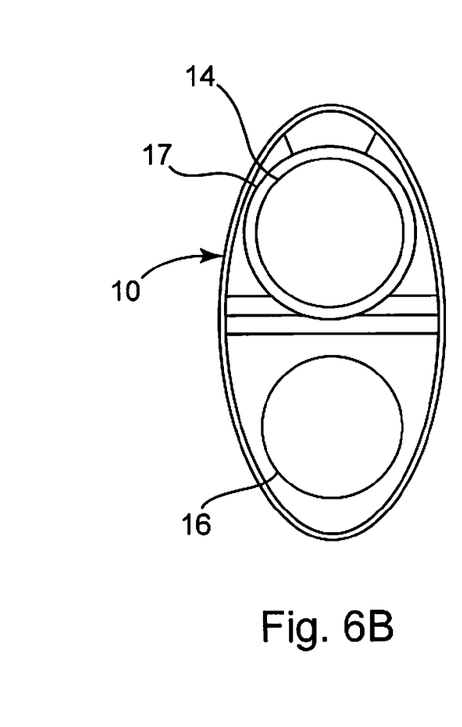

FIG. 6B shows a first alternative embodiment cross-section lumen configuration in which the lumen 14 is the arterial lumen and has a thinner wall 17. The thin lining of the arterial lumen provides sufficient rigidity to keep the catheter 10 open and also provides resistance to clotting. The venous lumen is relatively soft so that it may expand as the blood flow and venous pressure of the hemodialysis blood circuit is increased. The pliability of the venous lumen and the resulting expansion of the diameter of the venous lumen with increased blood flow aids in the reduction of the venous resistance within the catheter 10.

Figure 6C:
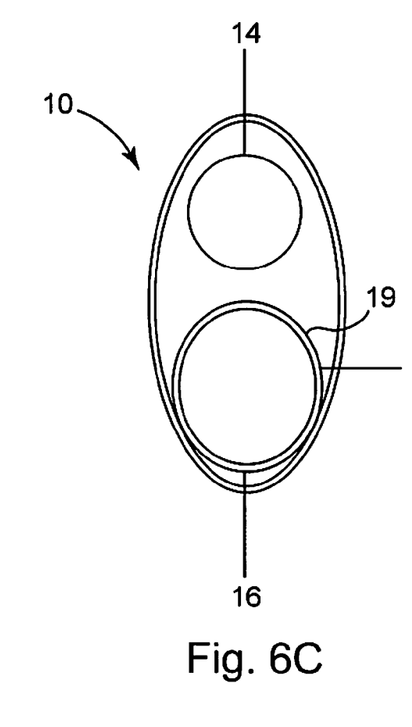

FIG. 6C shows a second alternative embodiment cross-section lumen configuration in which the arterial lumen 14 is larger than the venous lumen 16. The arterial lumen 14 contains a thin walled semi-rigid line 19, which may be made of polytetrafluoroethylene (TEFLON®) or other flexible bioinert material. Upon forced flow by the blood pump of the dialysis machine (not shown), the venous lumen 16 increases in size in relation to the blood flow.

Figure 6D:
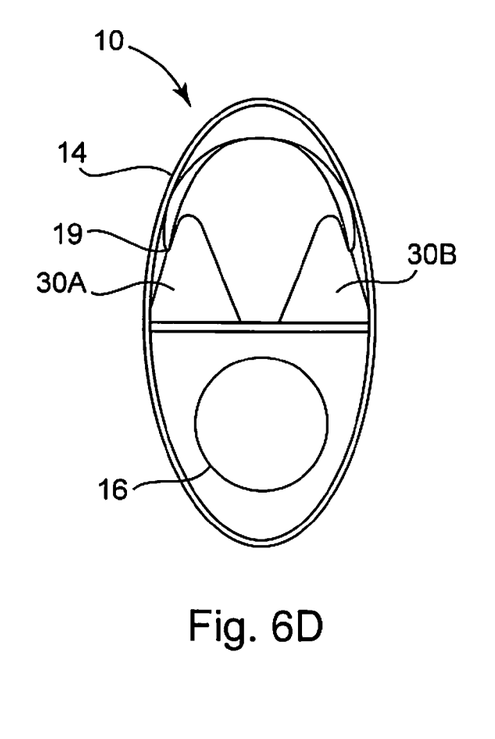

FIG. 6D shows a third alternative embodiment cross-section lumen configuration in which a thin lining 19 (made of material as described for liner 19 above) of the arterial lumen 14 provides sufficient rigidity to keep the catheter open as well as providing resistance to clotting. The venous lumen 16 is relatively soft so that it may expand as the blood flow and venous pressure of the hemodialysis blood circuit is increased. In this alternative embodiment, two bumper portions 30A and 30B are employed.

The first and second lumen segments 18, 20 are disjoined at a joint 31 to define a proximal Y-shaped portion 32 of the catheter 10. Each lumen 14 and 16 includes a distal lumen segment 33A and 33B, respectively and terminal end 34 and 36, respectively, and defines a respective opening 38 and 40. Each end 34 and 36 extends a sufficient length from the joint to permit easy and separate handling of each end during operative procedures by a surgeon. Each end 34 and 36 can preferably be fitted with a Luer lock or other locking fitting 42 and 44, respectively, which fitting may have external thread or flange 43.

Figure 7:
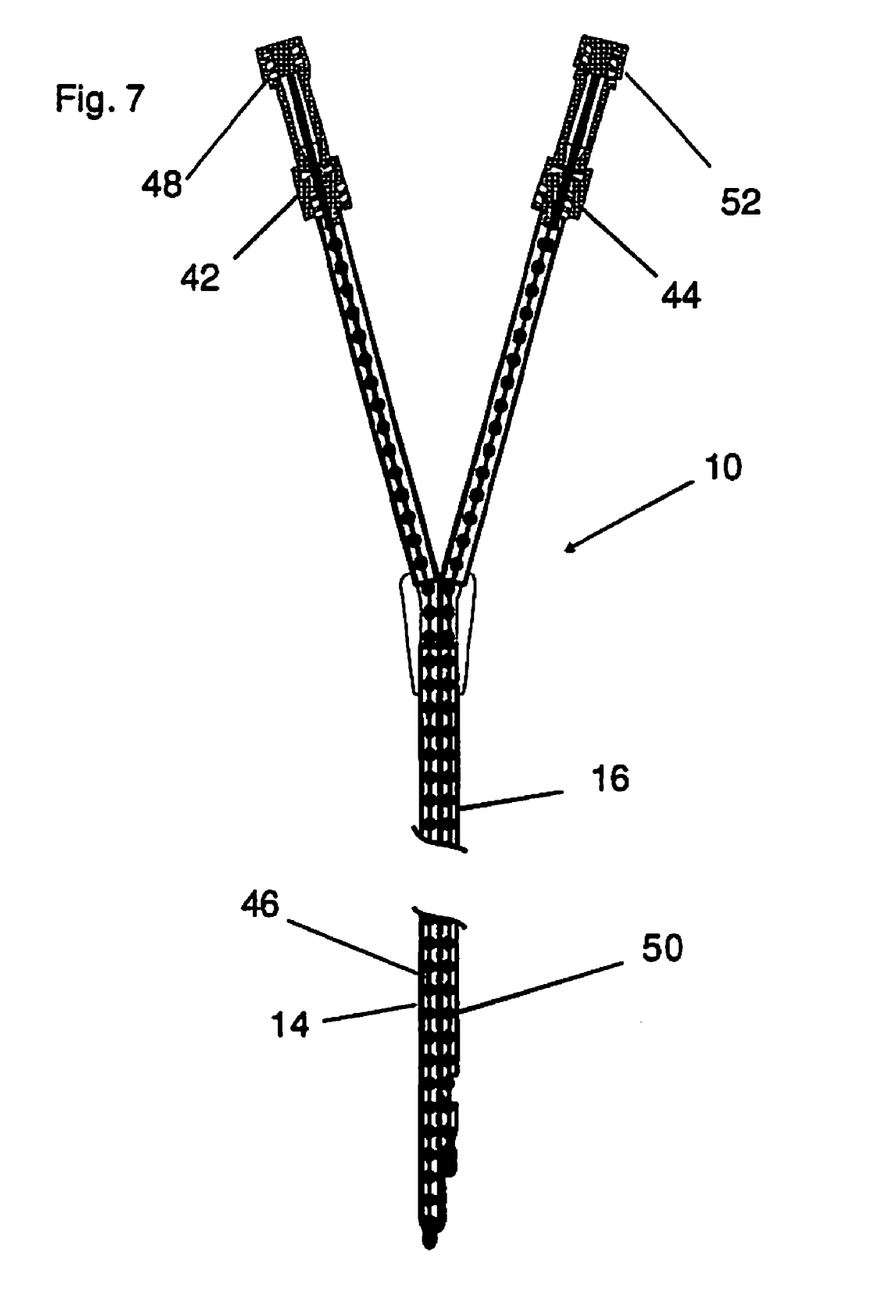
FIG. 7 shows the catheter of FIG. 1 with flexible rods therein.

As shown in detail in FIG. 7, the fittings 42, 44 also include a flexible leaf valve or a septum 45, which can occlude fluid backflow and reduce the risk of air embolism. An obturator (also referred to as an occluding) rod 46, 50 (shown in FIGS. 3 and 7) extends from an end cap 48, 52. Each end cap 48, 52 has internal thread 53 which threadingly mates with the flange 43. The rod 46 is inserted through the opening 40, through the leaf valve 45 in the fitting 44 and through the lumen segment 33A and into the distal lumen segment 18. The end cap 48 is fitted onto the fitting 42 and twisted to lock in position. Similarly, the rod 50 is inserted through the opening 38, through the leaf valve 45 in the fitting 44 and through the lumen segment 33B and into the distal lumen segment 20. The rods 46, 50 may be made of plastic, metal, or other material, or may be constructed of a metal wire core coated with plastic or other material or materials.

As can be seen in FIG. 7, the rods 46 and 50 can be a solid smooth surface, or, optionally include a bead-like outer surface which sealably abuts the inner wall of the lumens 14 and 16 to prevent air and fluid passage therethrough. Alternatively, the surface of the rod may have spaced protrusions or bumps of other regular or irregular geometric shapes. The obturator rods 46, 50 not only occlude the lumens 14, 16, but, when drawn in and out, also clear the lumens of any fibrin which may have accumulated in the lumen.

Disengageable clamps 54 and 56 are operably disposed about the proximal lumens segments 33A, 33B, respectively, as seen in FIG. 1.

The first end 22 can include one or more (preferably two) spaced axial cuffs (shown in one exemplary embodiment in FIG. 1 as two cuffs 58 and 60) which provide for tissue ingrowth therein to enable the catheter 10 to be suitably anchored within the body B and also to reduce the possibility of infection at the incision site.

A visible indicia 62 can preferably be formed or printed on the first end 22 between the cuffs 58 and 60 and the joint 31 (preferably about one centimeter from the cuff 58 nearest the joint 31) to serve as a position indicator of the cuffs 58 and 60 to the surgeon during the insertion procedure so as to provide an indication of the distal tip 26 of the catheter with respect to the cuff 58. Preferably, a suture wing 63 (known to those skilled in the art) is associated with the catheter 10, such as about the joint 31 area to enable the surgeon to suture the catheter to the patient to maintain the position of the catheter 10 and prevent undesirable movement.

In addition, the present invention provides for the tunneling device 12 (also known as an introducer), shown in FIG. 4 (with the catheter 10 in position) and FIG. 5 (with the catheter 10 removed) for use in inserting the catheter 10. The tunneling device 12 can be a single piece construction. The tunneling device 12 can be of a relatively rigid bioinert material having at least some degree of flexibility, such as, but not limited to, medical grade stainless steel or synthetic plastic, e.g., polyurethane, or the like. Alternatively, the material can be a wire filament core inside of a plastic/silastic material. The tunneling device 12 includes a handle 64 and a distal portion 66 which is of a length longer than the first end 22 of catheter 10 and is preferably configured with an exposed elongated channel 68 to receive the first end 22 of the catheter 10. Alternatively, the distal portion 66 may have a portion being a channel 68 and a portion being closed to form a conduit. The distal portion 66 is equipped with a hollow cap 70 to receive the openings 26 and 28 of the distal end 22 of the catheter 10 in a manner to maintain the openings 26 and 28 substantially covered during insertion of the catheter 10 into the body B, thereby preventing potential clogging thereof by tissue and blood. The cap 70 can be a bullet-like or other shape tip which can be threadably connected to the distal end 69.

Alternatively, at least a portion (preferably the distal end portion) of the cap 70 can have a geometric cross-section shape (e.g., square, hexagonal or the like) or may have a surface texture adapted (e.g., knurls, ribs, ridges, cross-hatching, grooves, rings, bumps, or other raised or surface treatments or etching (e.g. acid), or other loss method of creating the grooves, lines, etc.) to increase the surgeon's ability to grasp the tip 70 and unscrew it. The handle 66 may also optionally have a cross-sectional shape or surface treatment or texture as described for the cap 70 to similarly improve gripping by a (normally gloved) surgeon.

The channel 68 can be generally oval-shaped in cross-section as seen in FIG. 6 to accept the end 22. The tunneling device 12 preferably includes a mid-section 72 having a Y-shaped exposed channel 74 continuous with the exposed elongated channel 68 to receive at least part of the joint 31 and the lumen segments 33A and 33B. The tunneling device 12 of the present invention, and, particularly the rounded tip 70, shields the catheter tip 26 and pulls the tip 26 through the incision and opening more gently than currently available introducers.

Figure 8:
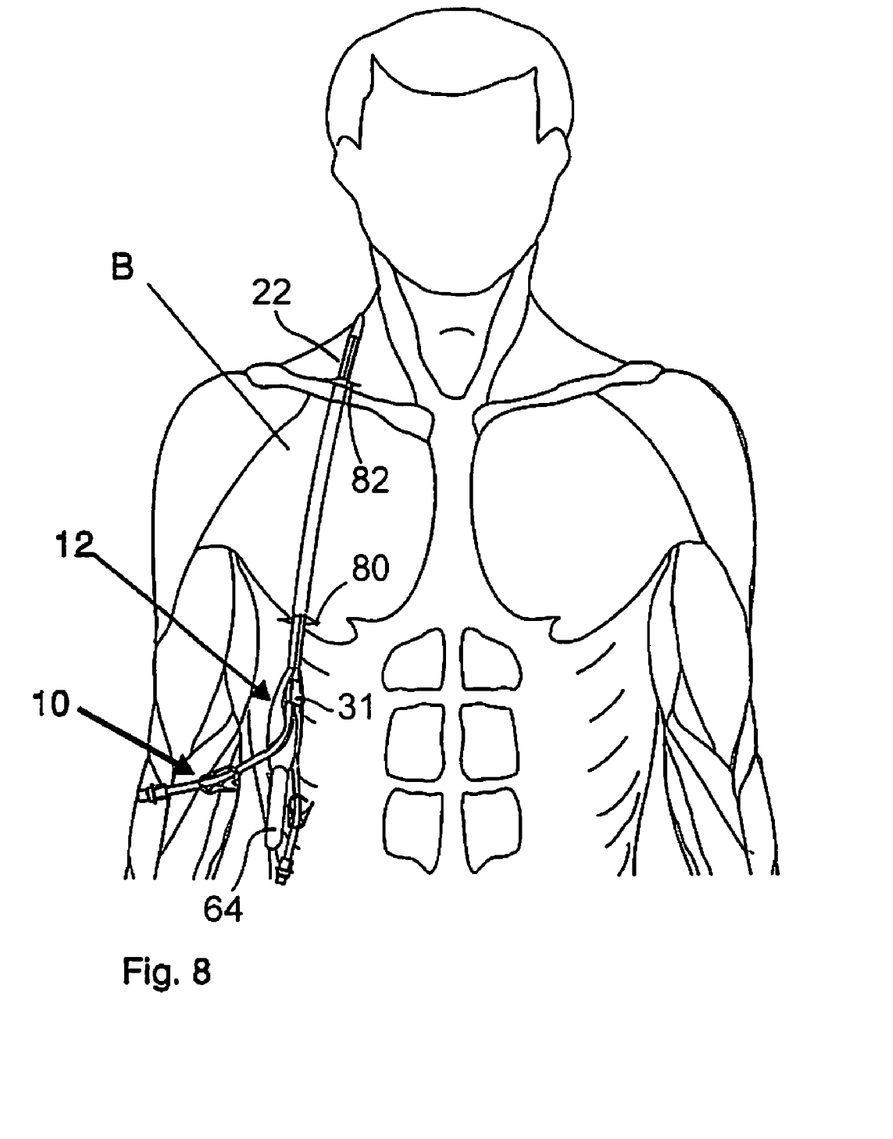
FIG. 8 shows a schematic view of the catheter and tunneling device of the present invention as inserted through an entrance incision and extending through an exit incision.
Figure 9:
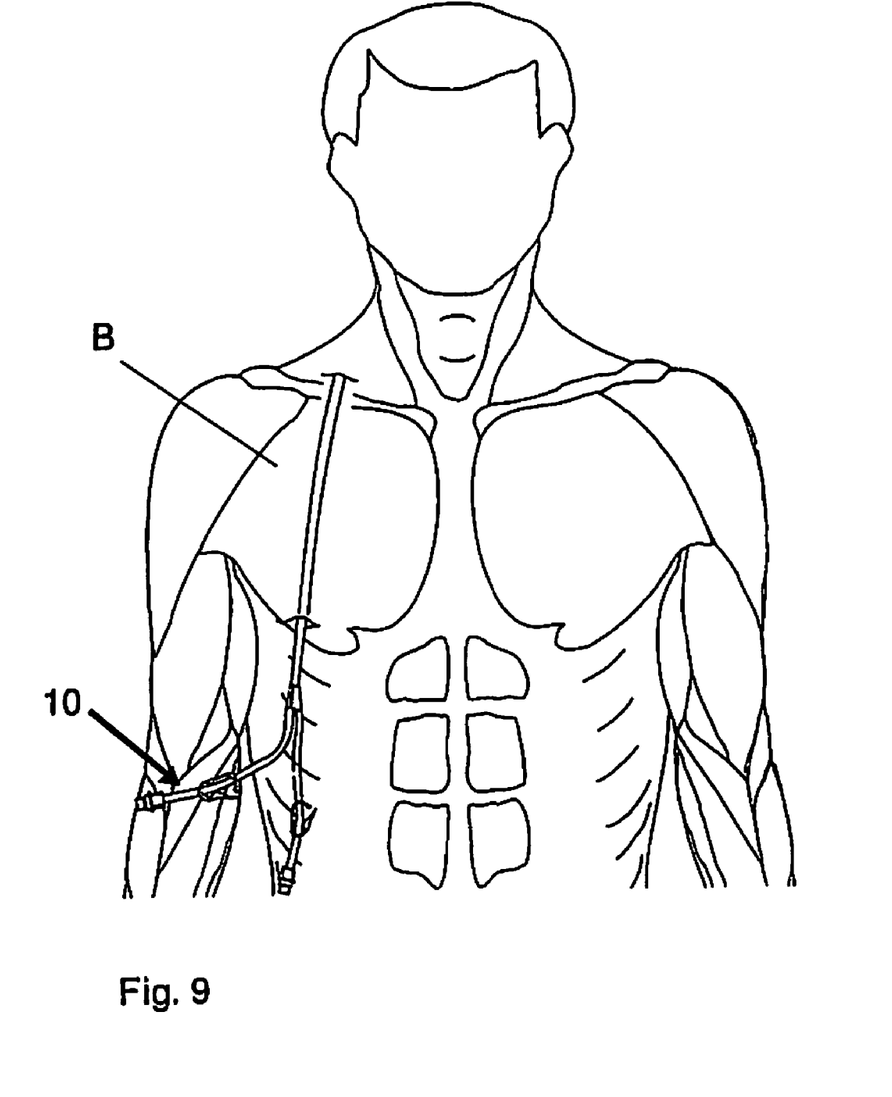
FIG. 9 shows a schematic view of the catheter as in FIG. 8, but with the tunneling device removed and the distal tip reinserted into the body through the exit incision.

The present invention also provides a method of introducing the catheter into a body, as shown in FIGS. 8 and 9. The catheter 10 and tunneling device 12 can come pre-packaged for a surgeon with the catheter 10 already loaded into the tunneling device 12. Once the surgeon has made the initial incision 80, the tunneling device 12 is inserted and advanced through the tissue of the body B to the second incision 82 at the internal jugular, the cap 70 is removed by unscrewing it from the tip 69. The surgeon grasps the handle 64 with one hand and the distal portion 22 with the other hand at the second incision 82, lifts the joint 31 area of the catheter 10 from the Y-shaped exposed channel 74 and slowly removes the tunneling device 12 back through the incision 80. The exposed elongated channel 68 of the tunneling device 12 allows it to slide over the catheter 10 as it is removed, thereby minimizing movement of the catheter 10 while in the body. A second introducer (not shown, but known to those skilled in the art) may be placed over the catheter tip 26 area and the tip area 26 is guided back into the second incision 82 and to the jugular or other target site in situ (see FIG. 9). The second introducer may be removed to leave the now indwelling catheter 10. The caps 48, 52 may be detached and the rods 46, 50 withdrawn from the lumens 14, 16. The septa 45 prevent backflow of blood or air. The fittings 42, 44 may be connected to a dialysis system, as is known in the art. The invention uses flexible rods 46 and 50 to displace the blood in the catheter lumens 14 and 16, when the catheter 10 is not being used. The tunneling device 12 is preferably intended for a single insertion. After it has withdrawn from the patient after use, it is disposed of. Alternatively, it may be possible to construct the device 12 of a sterilizable material and, under certain application, may be reused.

With the bumpers 30 (and variations) of the present invention the need for anticoagulants is substantially reduced or eliminated, thereby substantially reducing or eliminating the risk of hemorrhaging acute and chronic gastrointestinal bleeding, retinopathy, and anemia due to the use of indwelling anticoagulants to maintain the blood vessel wall open and fibrin-free at the catheter tip area. Further, the dual cuffs 58 and 60 provide for improved anchoring into the patient's tissue as well as provide blockage to motile bacteria wherein the indicia 62 indicates to the surgeon when the cuffs 58 and 60 are close to exiting the incision site.

Figure 10:
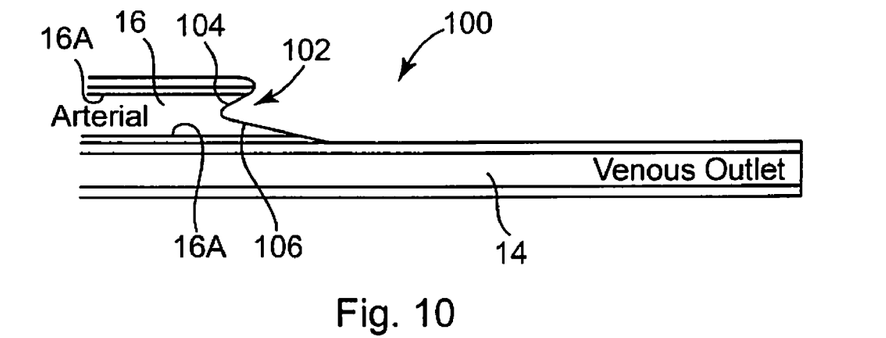
FIG. 10 shows a first alternative exemplary design of the bumper and tip area.
Figure 11:
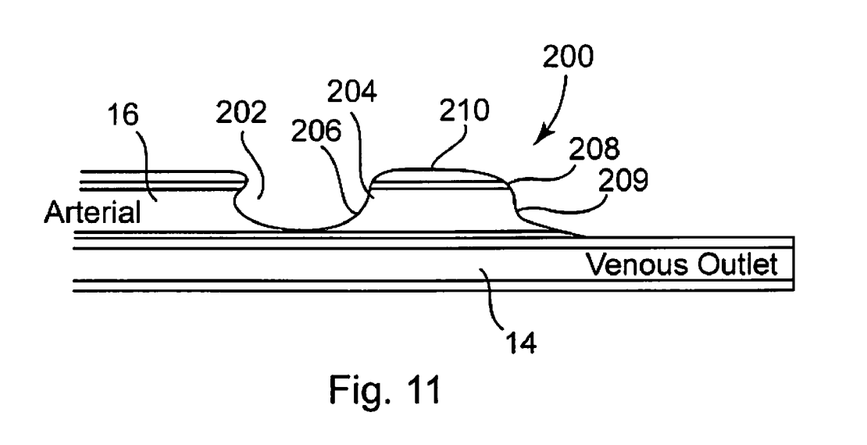
FIG. 11 shows second alternative exemplary design of the bumper and tip area.
Figure 12:
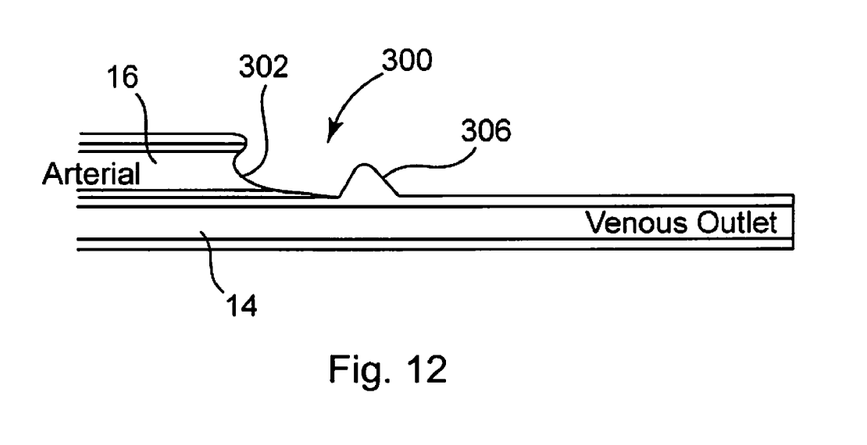
FIG. 12 shows a third alternative exemplary design of the bumper and tip area.

An important feature of the present invention is the design of the distal first end 22, as shown in FIG. 2. It is important to maintain flow of fluid at a high rate when desired. The bumper 30 maintains the blood vessel wall away from the opening 28. Also, the distal tip 22 design stabilizes the end 26 so that it maintains a relatively stable position generally near the axial center of the blood vessel and does not "whip" around within the blood vessel, which, among other detriments, can cause trauma or fatigue to the vessel wall. While FIG. 2 shows one preferred embodiment of the bumper 30, other designs are possible. A first alternative exemplary embodiment is shown in FIG. 10, which shows a distal tip 100 area with a venous lumen 14 and an arterial lumen 16, the arterial lumen 16 having an opening 102 which comprises a generally C-shaped opening having a first curved segment 104 and a second curved segment 106. Optionally, the inner wall 16A of the lumen 16 may have a thin lining or coating of a non-stick material, such as, but not limited to, polytetrafluoroethylene (TEFLON®). FIG. 11 shows a second alternative embodiment of a distal tip 200 area having lumens 14, 16 and an opening 202. A bumper 204 may have a hollow shape with openings 206 and 207 similar to the lumen 16 opening and may have a curved distal portion 208 and a flat top area 210 as shown in the drawing. FIG. 12 shows a third alternative exemplary embodiment of a distal tip 300 having an opening 302 comprised of a J-shaped curve. A bumper 304 comprises one or more bumps or protrusions 306. As in the embodiment of FIG. 10, the embodiments of FIGS. 2, 11 and 12 may be coated or lined as described.

With all the above described alternative embodiments, the blood vessel wall is maintained open and away from occluding the arterial lumen opening by the different bumper configurations.

The above described embodiments are set forth by way of example and are not for the purpose of limiting the present invention. It will be readily apparent to those skilled in the art that obvious modifications, derivations and variations can be made to the embodiment without departing from the scope of the invention. Accordingly, the claims appended hereto should be read in their full scope including any such modifications, derivations and variations.

What is claimed is:

1. A tunneling device for use in inserting a catheter, comprising:
   a relatively rigid member having a handle and an end configured with an elongated groove which extends radially inwardly from an outer surface of said rigid member and runs substantially lengthwise such that the groove is exposed and continuous and configured to laterally receive said catheter, wherein said groove further includes two separate channels forming a Y-shaped mid-section to receive at least part of a Y-shaped end of the catheter, wherein said end of said tunneling device is equipped with a hollow cap removably connected to a tip of said end of said tunneling device to receive a first end of said catheter and cover openings of the first end of the catheter in a manner to maintain the openings substantially covered during insertion of the catheter into a the body thereby preventing potential clogging thereof by tissue and blood and removed post insertion while the tunneling device remains in the body.

2. The tunneling device of claim 1, wherein said groove is generally oval shaped in cross section.

3. The tunneling device of claim 1, wherein said cap is threadably removably disposed on the tip of said end of said tunneling device.

4. A method of introducing a catheter into a body, comprising the steps of:
   a. providing a tunneling device comprising a relatively rigid member having a handle and an end configured with an elongated groove which extends radially inwardly from an outer surface of said rigid member and runs substantially lengthwise such that the groove is exposed and continuous and configured to laterally receive said catheter, wherein said groove further includes two separate channels forming a Y-shaped mid-section to receive at least part of a Y-shaped end of the catheter, wherein said end of said tunneling device is equipped with a removable hollow cap removably connected to a tip of said end of said tunneling device to receive openings of a first end of the catheter in a manner to maintain the openings substantially covered during insertion of the catheter into the body thereby preventing potential clogging thereof by tissue and blood;
   b. laying the first end of the catheter in the exposed elongated groove in a manner such that the openings of the first end of the catheter are received in the cap of the tunneling device;
   c. inserting the tunneling device having the catheter therein through a first incision of the body such that the cap extends out a second incision of the body;
   d. removing the cap post insertion while the tunneling device remains in the body;
   e. lifting the first end of catheter from the tunneling device;
   f. removing said catheter from the tunneling device; and
   g. removing said tunneling device from the body.

* * * * *